(12) United States Patent
Kim et al.

(10) Patent No.: US 10,005,716 B2
(45) Date of Patent: Jun. 26, 2018

(54) METHOD FOR SYNTHESIZING CATECHOLAMINES BY USING PLASMA POLYMERIZATION

(71) Applicant: Cheorwon Plasma Research Institute, Gangwon-do (KR)

(72) Inventors: Steven Kim, Seoul (KR); Deuk Yeon Lee, Gyeonggi-do (KR); Hae Shin Lee, Daejeon (KR); Young Chang Seo, Daejeon (KR)

(73) Assignee: CHEORWON PLASMA RESEARCH INSTITUTE, Gangwon-Do (KR)

( * ) Notice: Subject to any disclaimer, the term of this patent is extended or adjusted under 35 U.S.C. 154(b) by 0 days. days.

(21) Appl. No.: 15/115,937

(22) PCT Filed: Feb. 9, 2015

(86) PCT No.: PCT/KR2015/001284
§ 371 (c)(1),
(2) Date: Aug. 2, 2016

(87) PCT Pub. No.: WO2015/119469
PCT Pub. Date: Aug. 13, 2015

(65) Prior Publication Data
US 2017/0158609 A1     Jun. 8, 2017

(30) Foreign Application Priority Data

Feb. 7, 2014  (KR) .................. 10-2014-0014462
Feb. 9, 2015  (KR) .................. 10-2015-0019330

(51) Int. Cl.
C07C 215/52    (2006.01)
C07C 215/60    (2006.01)
C07C 213/02    (2006.01)
C07C 213/00    (2006.01)
C07C 223/02    (2006.01)

(52) U.S. Cl.
CPC .......... *C07C 215/52* (2013.01); *C07C 213/00* (2013.01); *C07C 213/02* (2013.01); *C07C 215/60* (2013.01); *C07C 223/02* (2013.01)

(58) Field of Classification Search
None
See application file for complete search history.

(56) References Cited

PUBLICATIONS

International Search Report from Corresponding Application No. PCT/KR2015/001284; dated Apr. 21, 2015.
Ball et al.; "Deposition Mechanism and Properties of Thin Poly dopamine Films for High Added Value Applications in Surface Science at the Nanoscale"; BioNanoSci.; 2012, 2; pp. 16-34.
Abourayana, et al.; "Synthesis and Characterization of Plasma Polymerized Thin Films Deposited from Benzene and Hexamethy Idisiloxane using (PECVD) Method"; World Academy of Science, Engineering and Technology; vol. 5 Feb. 26, 2011; pp. 253-259.

(Continued)

*Primary Examiner* — Clinton A Brooks
(74) *Attorney, Agent, or Firm* — Pearne & Gordon LLP

(57) ABSTRACT

A method is provided for preparing a catecholamine-based compound by using plasma polymerization, and more specifically, to a method for artificially synthesizing various catecholamines, that is, monomolecular compounds capable of having a hydroxyl group (—OH) as an ortho group of a benzene ring and various alkylamines as a para group thereof from a catecholamine precursor material such as phenol or aniline by using dry plasma polymerization.

8 Claims, 10 Drawing Sheets

(56) References Cited

PUBLICATIONS

Cruz et al.; "Synthesis of polyaniline films by plasma polymerization"; Synthetic Metals; 1997, 88; Dated 213-218.
Ku, et al.; "General functionalization route for cell adhesion on non-wetting surfaces"; Biomaterials; 31 (210); pp. 2535-2541.
Ryu, et al.; "Catechol-Functionalized Chitosan/Pluronic Hydrogels for Tissue Adhesives and Hemostatic Materials"; Biomactomolecules; 2011, 12; pp. 2653-2659.

[FIG.1]
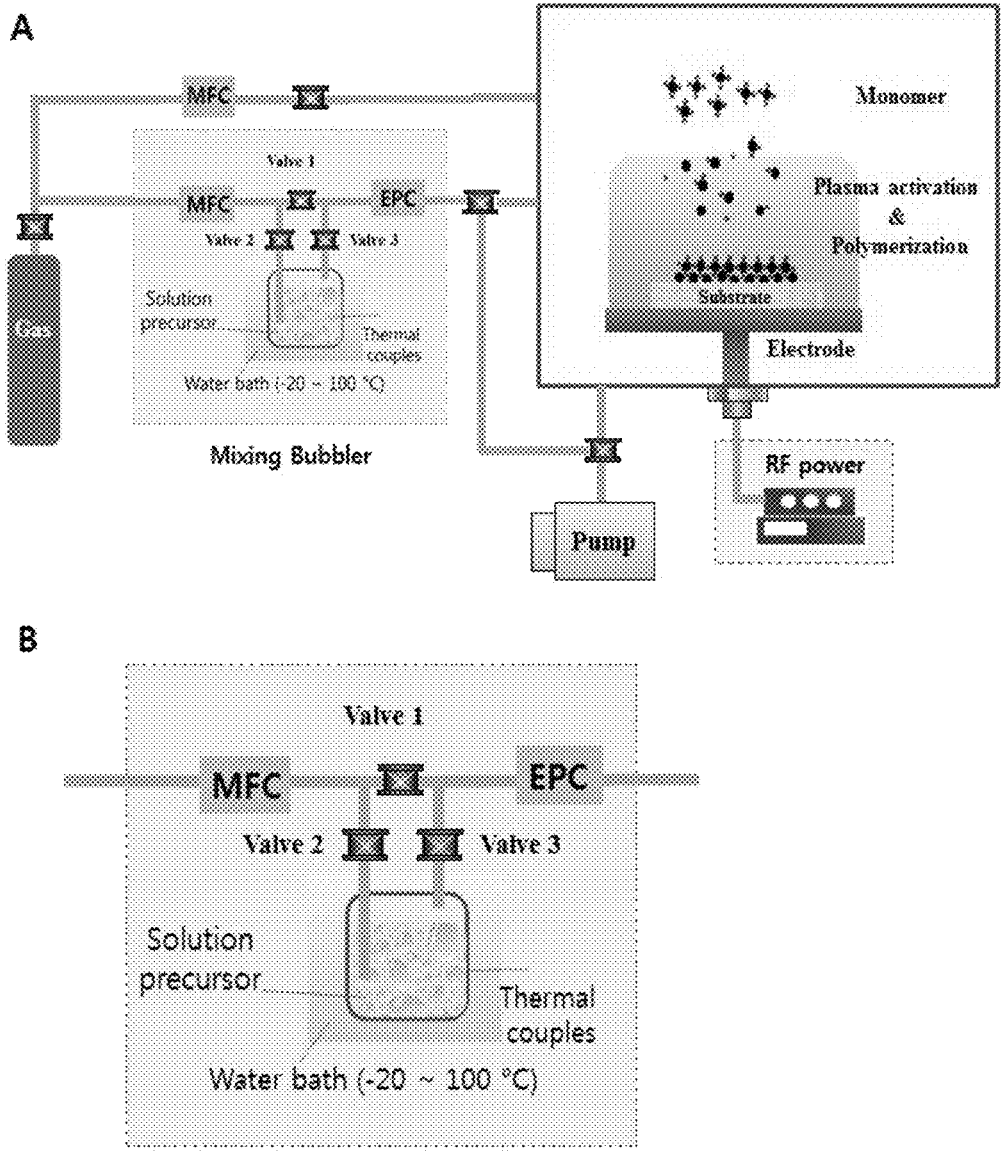

[FIG.2]
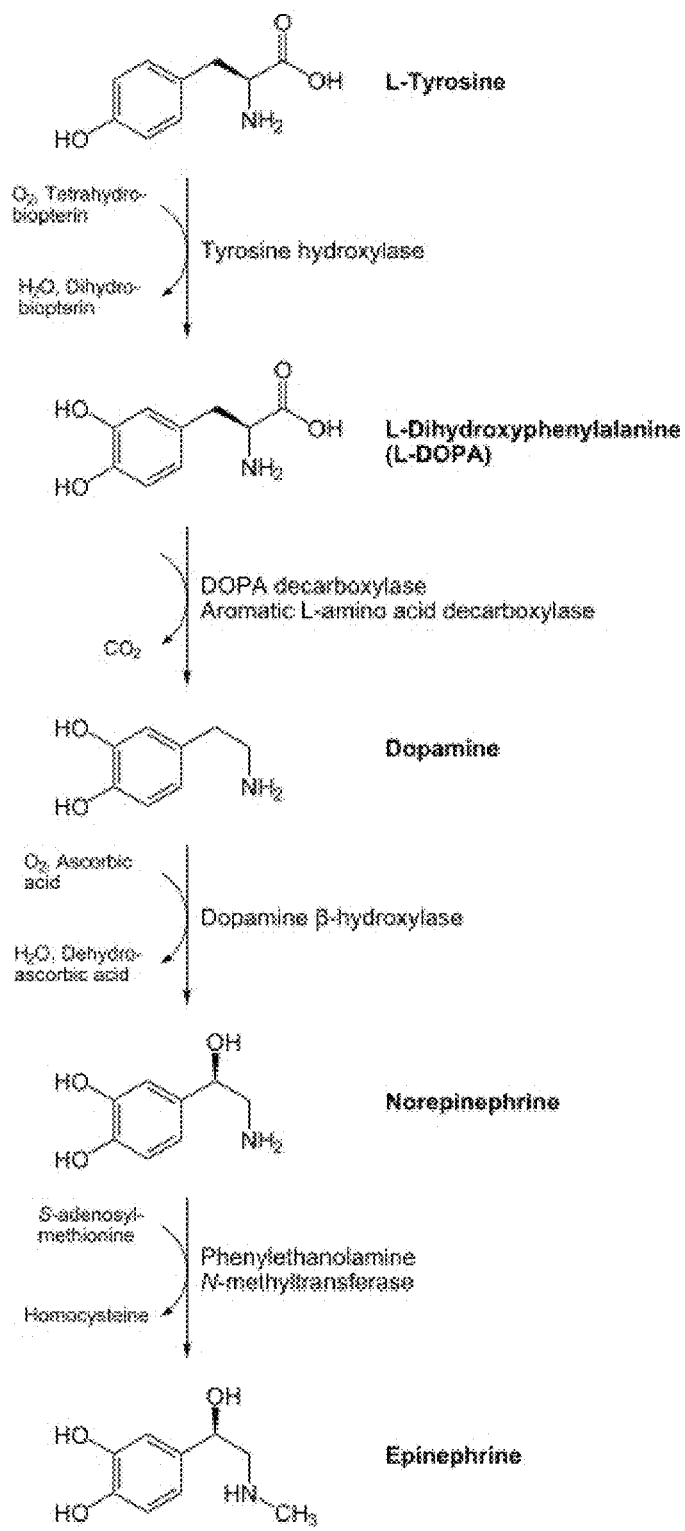

[FIG.3]
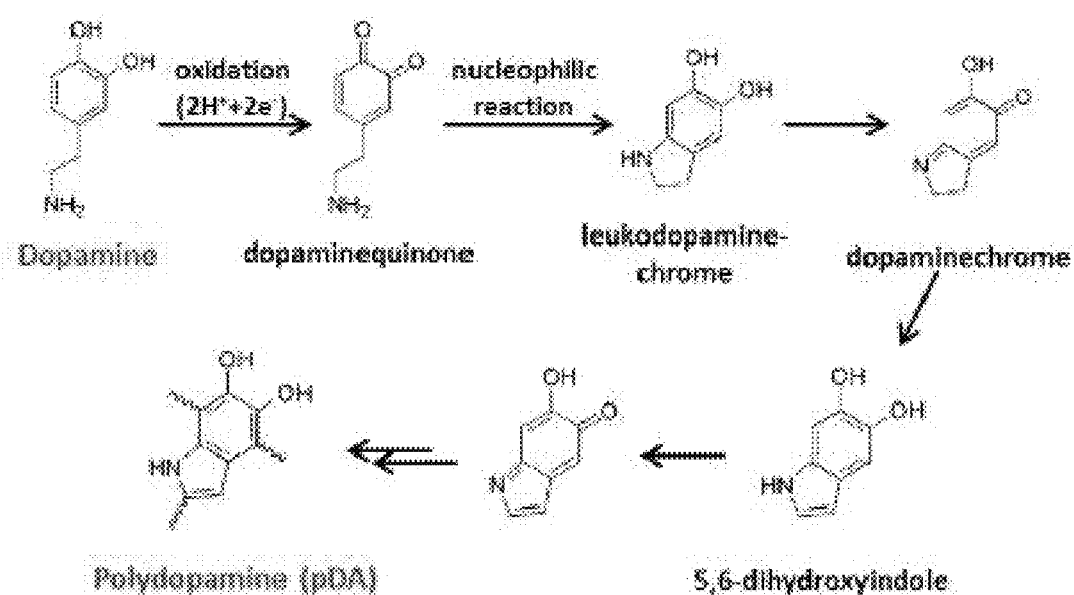

[FIG.4]
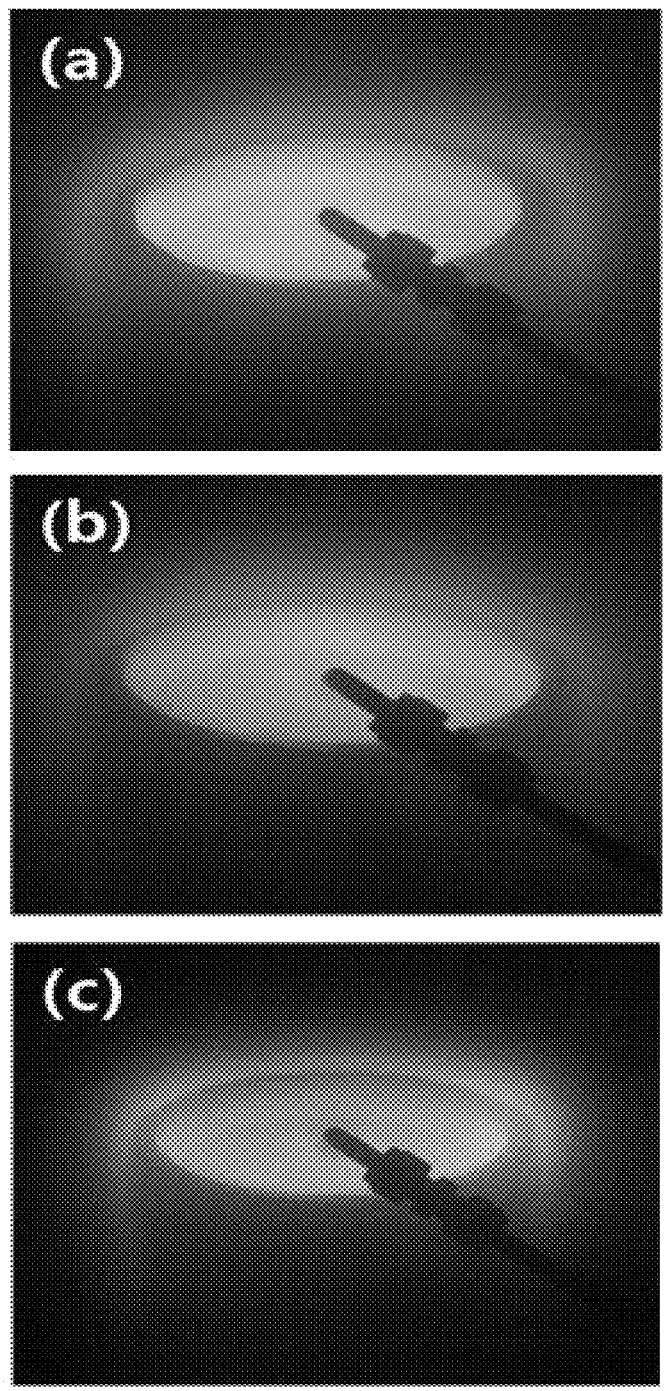

[FIG.5]
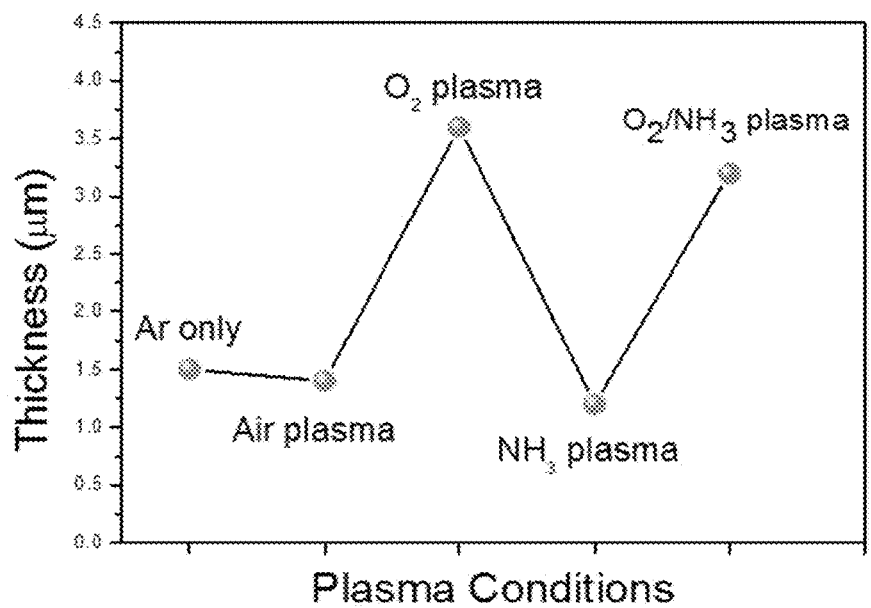
[FIG.6]
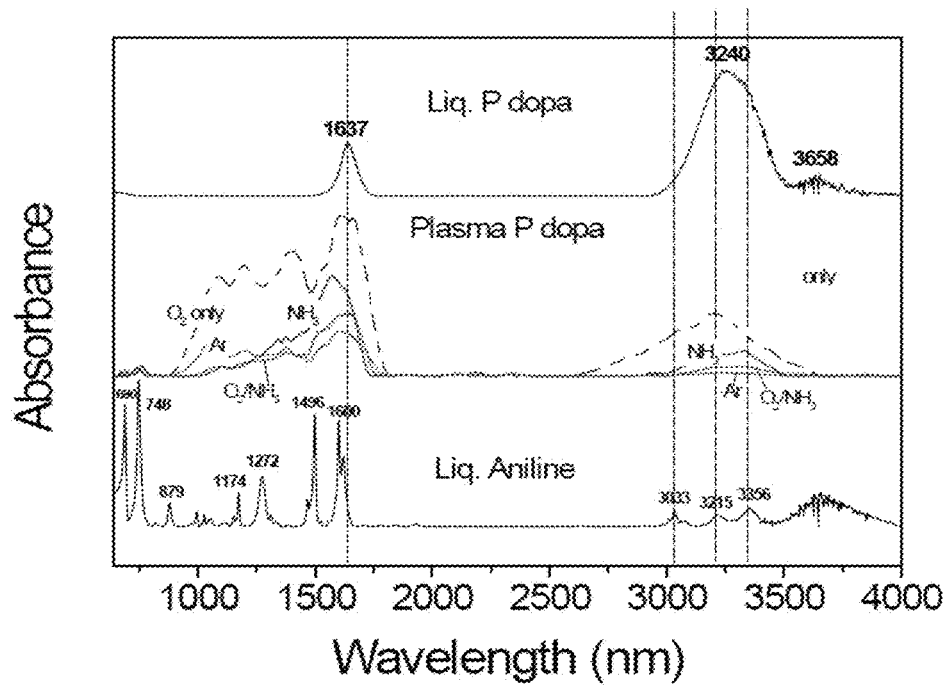

[FIG.7]
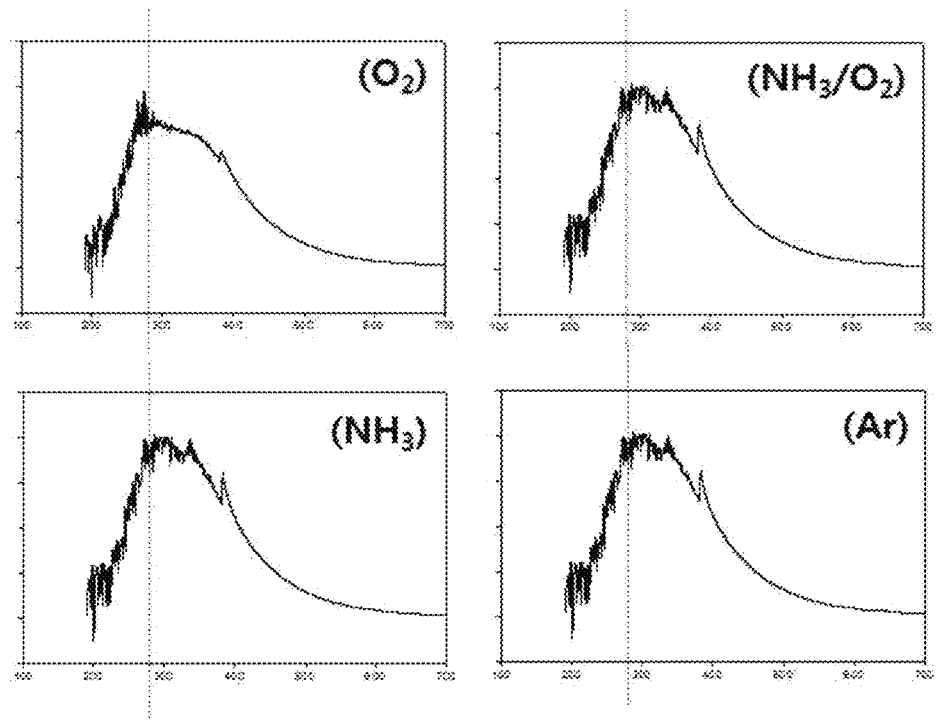
[FIG.8]
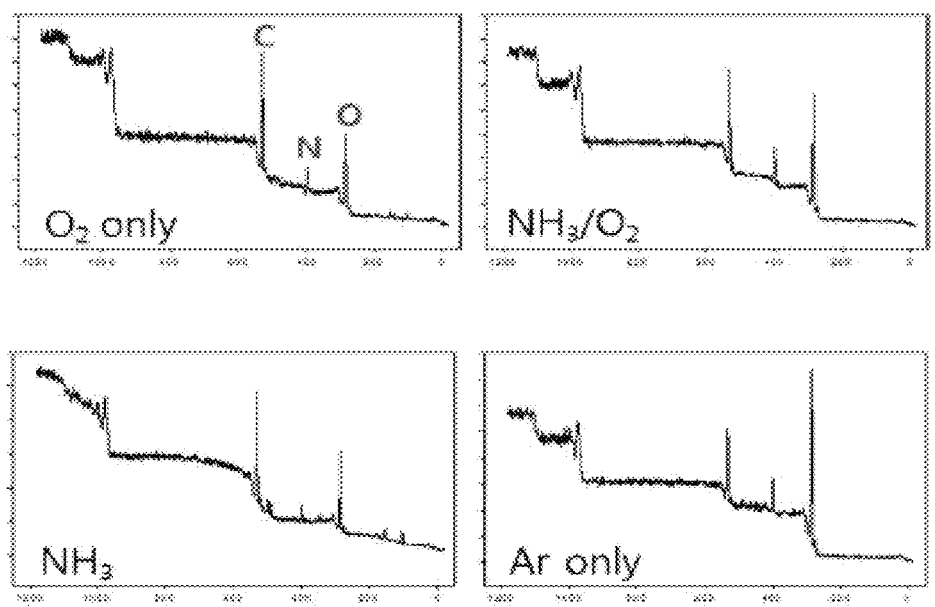

[FIG.9]
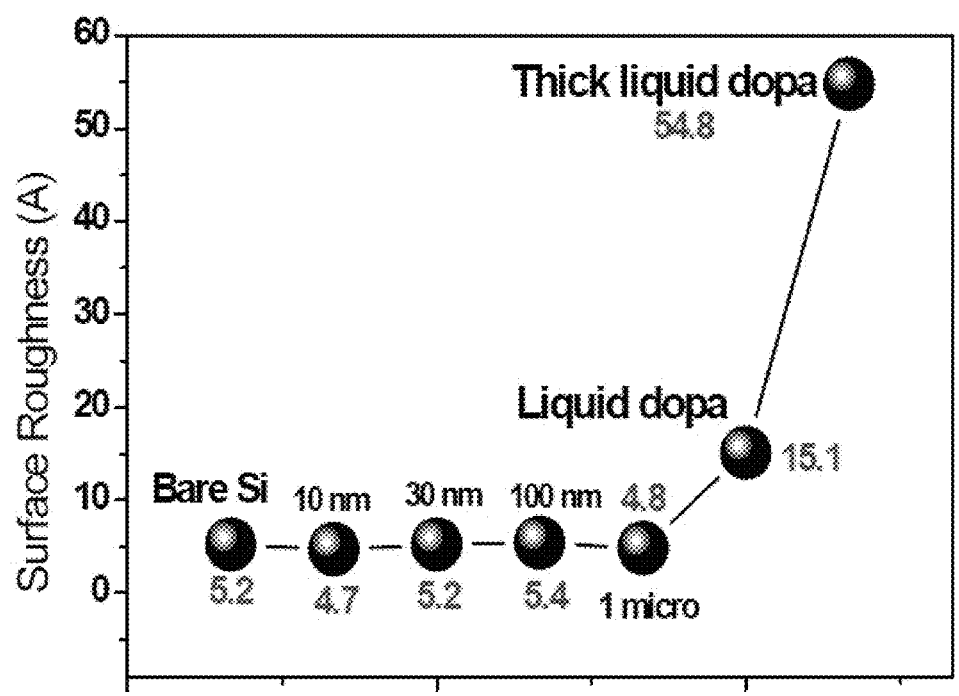

[FIG.10]
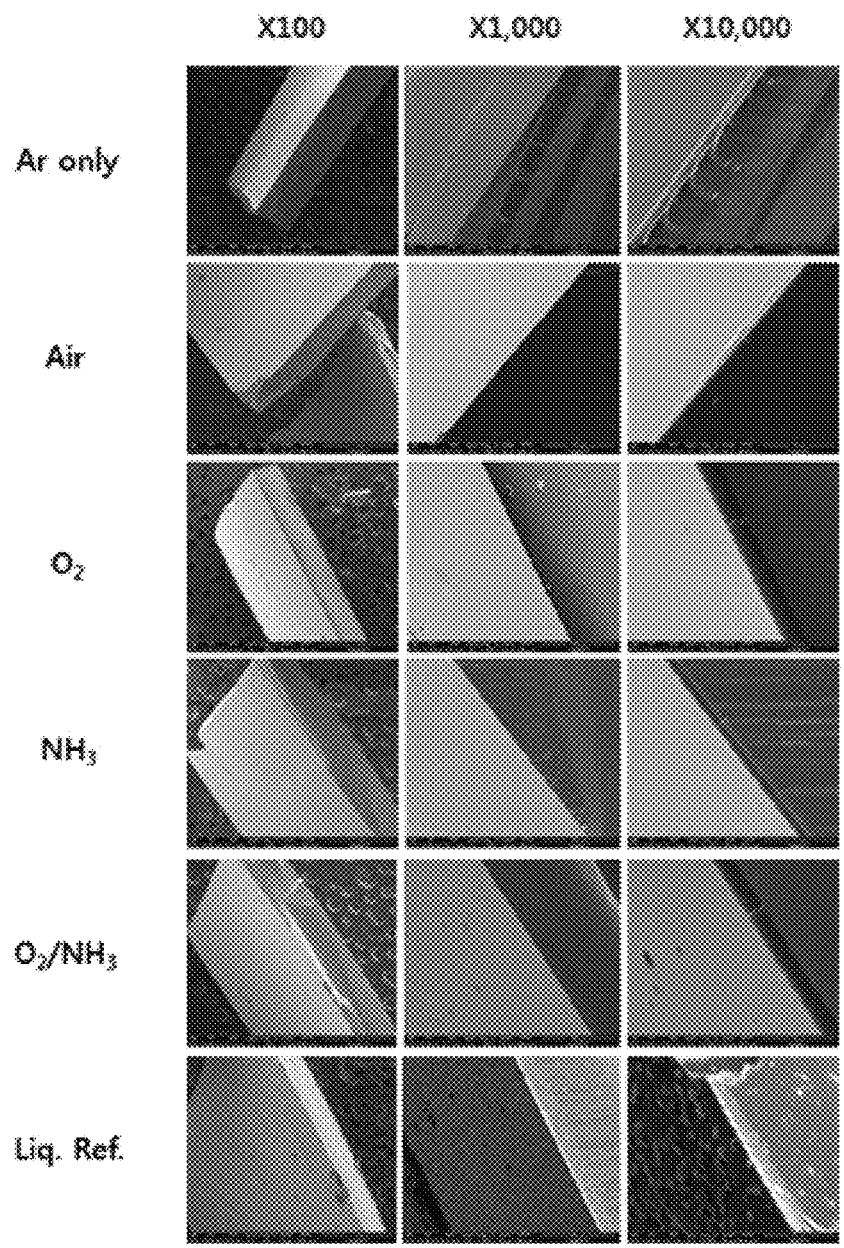

[FIG.11]
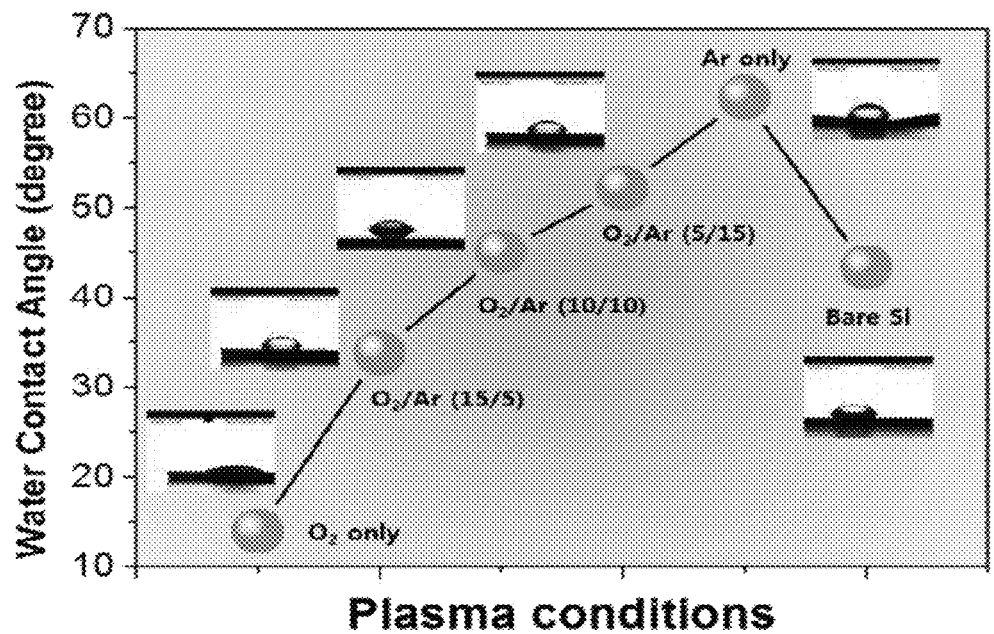
[FIG.12]
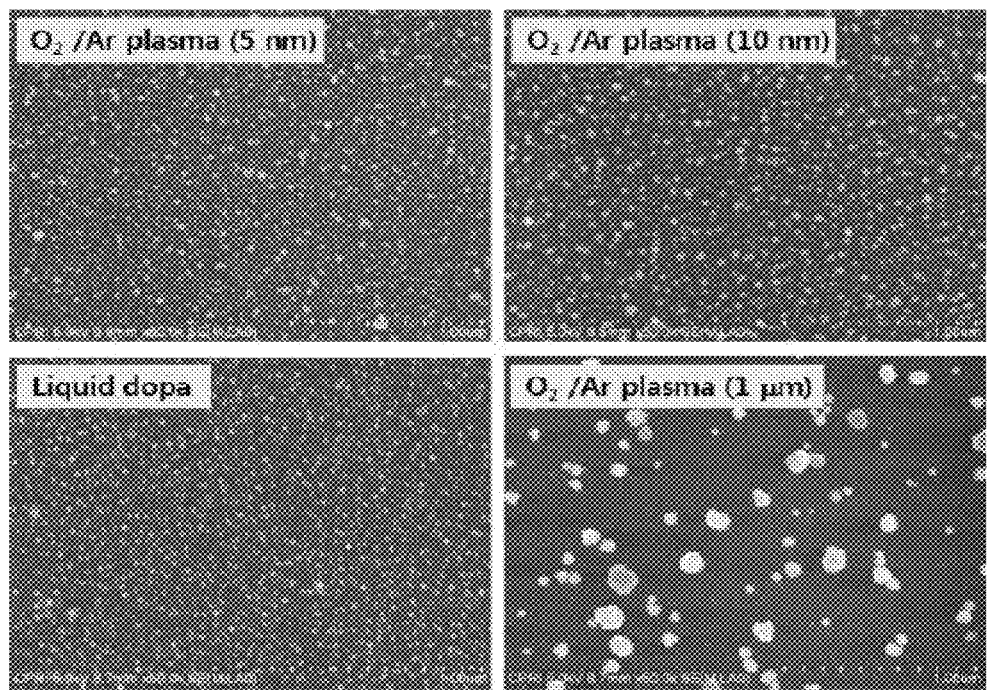

[FIG.13]
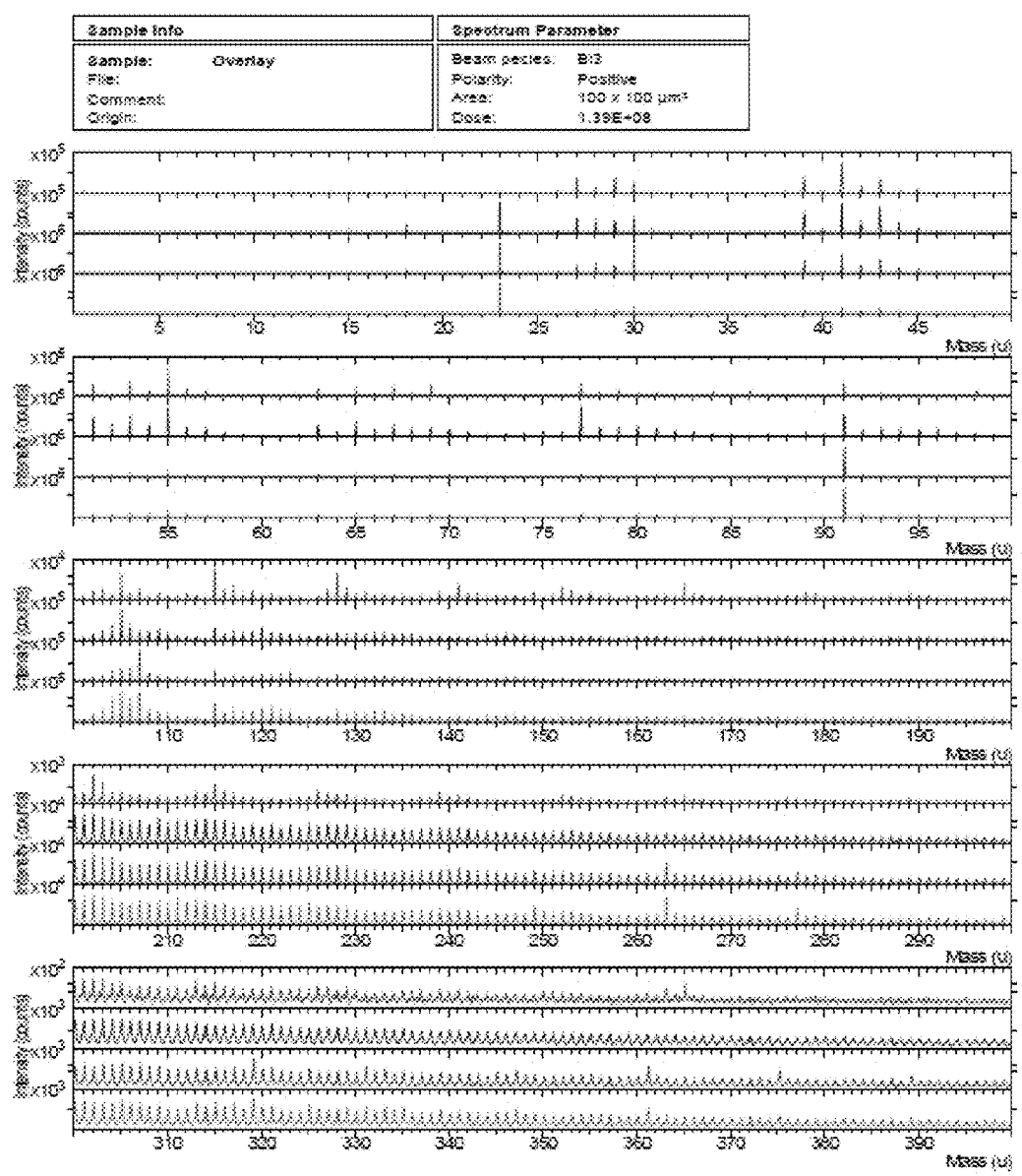

METHOD FOR SYNTHESIZING CATECHOLAMINES BY USING PLASMA POLYMERIZATION

TECHNICAL FIELD

The present invention relates to a method for synthesizing catecholamine-based compounds by using a plasma polymerization method, and more particularly, to a method for synthesizing various catecholamines, that is, monomolecular compounds capable of having a hydroxyl group (—OH) as an ortho group of a benzene ring and various alkylamines as a para group thereof from a catecholamine precursor material such as aniline by using a dry plasma polymerization method.

BACKGROUND ART

Recently, the brilliant developments of vacuum technique give an impetus to the commercialization of various advanced technologies using vacuum. In particular, plasma processes show the remarkable growth and are extensively used in the manufacturing and processing of various materials throughout the whole industry.

Plasma polymerization is one of such plasma processes and is technique using the coating phenomenon of a polymer material produced during the conversion of gases and organic vapors to plasma at a low pressure to coat a solid surface with the polymer material as a thin film.

This phenomenon was found by chance during studying plasma using electrical discharge in 1950s, however did not attract attention for a long time, but attracts attention as a novel method for synthesizing a polymer after identifying that the material thus produced is a polymer material only until 2008.

Meanwhile, a polydopamine was firstly reported as an adhesive polymer imitating the adhesive mechanism of a mussel adhesive protein in 2007s. As the polydopamine is known to be coated on almost all organic materials, inorganic materials such as metals, ceramics, semiconductor materials, and synthetic polymers in an aqueous solution under oxidation conditions to form an active surface, the polydopamine receives attention in various technical fields. Since the material is imitated from mussels, the biocompatibility thereof is very good, and the material may be coated on almost all surfaces. Since the coated surface is active, a novel material may be introduced onto the polydopamine coating. In the case of applying the polydopamine to various synthetic polymers/natural polymers, the polymers also have adhesiveness and coating ability, and may be applied in various techniques.

For example, it is reported that cell cultivation may become possible by introducing the polydopamine coating on a surface to which cell cannot be attached such as polyethylene, silicon rubber and PDMS (S. H. Ku et al., Biomaterials 2010, 31, 2535). An adhesive chitosan hydrogel is formed by introducing polydopamine to chitosan which is a natural polymer and is actively studied as a polymer for medical use, and a hemostatic using the same was developed (J. H. Ryu et al., Biomacromolecules 2011, 12, 2653). Besides, the polydopamine is introduced to typical polymers for medical use, which includes hyaluronic acid, polyethylene glycol (PEG), etc. to develop an adhesive polymer for diversely applying the same in medical/bio fields for modifying a biocompatible surface, for forming hydrogel, etc.

In addition, application study on the polydopamine in an energy field also receives attention, and adhesiveness is imparted by introducing the polydopamine to a polymer such as arginic acid, and polyacrylic acid, which are used as the binder of a lithium ion battery, and the adhesiveness between a binder and an electrode may be improved, thereby significantly increasing the capacity and the life of the battery.

The polydopamine may be biosynthetically obtained from DOPA which is a material playing the core role in the function of the adhesive protein of a mussel. In FIG. 2, the biosynthetic process of such catecholamine is schematically illustrated.

"DOPA" is a precursor material produced during the biosynthesis of catecholamine, and tyrosine which is an amino acid is converted to L-DOPA in catechol series by tyrosine hydroxylase. DOPA is the abbreviation of 3,4-dihydroxy-L-phenylalamine and is also called as L-DOPA (levo DOPA or L-3,4-dihydroxyphenylalamine). A DOPA material may be purchased and used, and is generally purchased as a powder shape.

However, until now, the polydopamine is used as an aqueous solution of a commercially available DOPA powder or by the self polymerization of dopamine formed in a mixture solution of an aqueous solution and an organic solution, or may be extracted from an organism such as a mussel. However, the application of the polydopamine for the surface modification by dry plasma polymerization has not been reported. That is, the polydopamine has not been used through artificial synthesis via plasma polymerization.

The inventors of the present application found that a catecholamine compound such as polydopamine may be synthesized by using aniline, etc., as a starting material not by the conventional dip-coating method but by a dry plasma polymerization process, and the catecholamine thus synthesized has a uniform thin film shape and has effective surface modification effects at the same time, and completed the present invention.

DISCLOSURE

Technical Problem

The present invention provides a method for synthesizing a catecholamine-based compound by using plasma polymerization, and a use thereof.

The present invention also provides effective conditions of a plasma polymerization process which is used for performing a plasma polymerization reaction for synthesizing catecholamine compounds.

The present invention also provides various uses of the catecholamine thus synthesized.

Technical Solution

According to an aspect of the present invention, there is provided a method for synthesizing a catecholamine using a plasma polymerization method and using at least one compound selected from the group consisting of benzene, aniline, phenol, benzylamine, phenethylamine, pyrocatechol, 2-hydroxypyridine, 3-hydroxypyridine, 4-hydroxypyridine, anthracene, naphthalene, 2-naphthol, 9-anthracenol, 2-anthracenol, and 1-anthracenol as a starting material. Preferably, the benzene, the phenol, or the aniline, and the most preferably, the aniline may be used.

The catecholamine obtainable by the method of the present invention may be synthesized in various types according to the selection of precursor materials, and for example, may be selected from the group consisting of dopamine, dopamine-quinone, alpha-methyldopamine, norepinephrine, epinephrine, alphamethyldopa, droxidopa, and 5-hydroxydopamine. In an embodiment of the present invention, dopoamine may be synthesized from aniline and then, polydopamine may be obtained.

Particularly, the plasma polymerization method of the present invention may be a dry plasma polymerization method, and the catecholamine thus synthesized may be formed as a thin film shape. That is, the catecholamine may be synthesized as the thin film and a target solid may be coated therewith, simultaneously. Accordingly, the plasma polymerization method of the present invention may be favorably applied in diverse technical fields in which the modification of a surface with catecholamines is necessary.

The dry plasma polymerization method may use an argon or nitrogen gas as a carrier gas; and at least one gas selected from the group consisting of hydrogen, nitrogen, oxygen, vapor, ammonia, and a mixture gas thereof as an activating gas. Preferably, the oxygen or the ammonia gas may be used, and the most preferably, the oxygen gas may be used.

In addition, the dry plasma polymerization method may be conducted under radio frequency (RF) power conditions of a high frequency range of 0-200 W, and preferably, under RF power conditions of a high frequency range of 50 W; and under pressure conditions of $1 \times 10^{-3}$ to $5 \times 10^{-1}$ torr, and preferably, under pressure conditions of $1 \times 10^{-1}$ torr for about 1-100 minutes, and preferably, for 1-60 minutes.

The catecholamine synthesized by the above method may have a thin film thickness of about 0.1-2 μm.

In an embodiment of the present invention, a polydopamine thin film having a thickness of about 1 micrometer is formed by a dry plasma polymerization method using aniline as a precursor material, and using oxygen as an activating gas, and under the conditions of an RF power of a high frequency range of 0-100 W, and a pressure of $1 \times 10^{-2}$ to $5 \times 10^{-1}$ torr. The polydopamine thus obtained may have an FTIR peak of 3240 cm$^{-1}$ and a UV absorption peak between 280 nm and 350 nm. Particularly, the polydopamine synthesized by the plasma process of the present invention may have a more planar surface, for example, the same degree as an Si wafer substrate, when compared to polydopamine synthesized by the conventional dip coating method.

In addition, there are provided in the present invention a catecholamine compound artificially synthesized using the plasma polymerization method of the present invention, and diverse uses thereof.

Advantageous Effects

As described above, a novel method for effectively synthesizing a catecholamine compound not by the conventional dip-coating method but by a dry plasma polymerization process may be provided in the present invention. In particular, the synthetic rate is fast by hundred times or more, and since the method uses a dry process, the method may be applied in diverse fields in which an aqueous solution is not used, and may be applied for mass production. In addition, unique properties such as very planar surface different from catecholamine (for example, dopamine) synthesized in an aqueous solution state may be obtained, and various surfaces may be functionalized by plasma, and the method may be usefully applied in wide ranges over a bio field, an energy field, an environment field, etc.

DESCRIPTION OF DRAWINGS

The patent or application file contains at least one drawing executed in color. Copies of this patent or patent application publication with color drawings will be provided by the Office upon request and payment of the necessary fee.

FIG. 1 is a schematic diagram of a plasma polymerization apparatus and a process (A) and a mixing bubbler used in the method of the present invention.

FIG. 2 is a schematic diagram of a biosynthetic process of catecholamines.

FIG. 3 is a schematic diagram illustrating structural change according to the oxidation reaction of dopamine and the forming step of polydopamine.

FIG. 4 is results obtained by observing the plasma color according to the kind of activating gases.

FIG. 5 is a graph obtained by observing the thickness of a polymerized film after deposition under different plasma conditions with an RF power of 50 W for 30 minutes.

FIG. 6 is a graph obtained by analyzing through ATR FTIR, the chemical bonding state of a sample produced via dopamine plasma polymerization in various plasma gas conditions using an aniline liquid phase precursor.

FIG. 7 illustrates UV absorbance analysis results of a polymerized film in various plasma conditions using the aniline of the present invention as a liquid phase precursor.

FIG. 8 illustrates XPS wide scan and quantitative analysis of synthesized polydopamine using the aniline of the present invention in a liquid phase precursor.

FIG. 9 illustrates surface roughness measured in 1,000 .mu.m (1 .mu.m resolution) region using a profilometer (.alpha. step) with respect to polymerized polydopamine.

FIG. 10 illustrates HRSEM analysis results with an inclined angle observed after making a cross-section in an Si wafer for observing the surface shape of the films synthesized by different plasma conditions.

FIG. 11 illustrates the measured results of water contact angle for polydopamine samples synthesized in various plasma process conditions using the aniline liquid phase precursor of the present invention.

FIG. 12 illustrates HRSEM analysis results according to the thickness (5, 10 nm, 1 .mu.m) of synthesized polymer films formed in mixed plasma conditions of oxygen and argon (15/5) in 50 mL of an AgNO.sub.3 solution.

FIG. 13 illustrates SIMS analysis results of polydopamine polymerized in oxygen plasma conditions using aniline, polydopamine polymerized in a liquid phase, and polydopamine polymerized using a liquid precursor of benzylamine, or penethylamine.

BEST MODE FOR CARRYING OUT THE INVENTION

Until now, biosynthesized catecholamine was obtained via extraction from living organisms, or catecholamine such as dopamine was obtained from DOPA, etc., which is a precursor material derived from living organisms using a dip-coating method. However, the compounds of diverse catecholamines such as dopamine, norepinephrin, and epinephrine could not artificially synthesized directly using specific precursor materials which may be easily synthesized.

The present invention relates to a method for preparing a catecholamine compound using a plasma method, and more particularly, to a method of artificially synthesizing catecholamines from various specific catecholamine precursors using a dry plasma polymerization method.

That is, there is firstly provided in the present invention a method of artificially synthesizing catecholamine compounds not using a precursor material derived from living organisms such as DOPA but using an artificially synthesized precursor material and a plasma polymerization method.

Hereinafter, the present invention will be explained in more detail.

Starting Materials

As starting materials for synthesizing catecholamine compounds, materials easily synthesized or produced by a person skilled in the art may be used as the precursor materials of the catecholamine in the present invention.

In order to synthesize polydopamine via plasma polymerization, two of a catechol (OH) functional group and an amine (NH2) functional group are required to be synthesized in a benzene ring which is the basic structure of dopamine. The merit of the present invention is the formation of the functional groups, respectively, in a benzene structure by controlling plasma chemical conditions.

The liquid precursor used in the present invention may include the combination of catechol and amine, a carbon bridge, or various materials according to the number of the benzene ring.

For example, at least one compound selected from the group consisting of benzene which is the basic structure, aniline, phenol, benzylamine, phenethylamine, pyrocatechol, 2-hydroxypyridine, 3-hydroxypyridine, 4-hydroxypyridine, anthracene, naphthalene, 2-naphthol, 9-anthracenol, 2-anthracenol, and 1-anthracenol, may be used as the precursor material of the catecholamines. Preferably, benzene, aniline, phenol, benzylamine, penethylamine, pyrocatechol, anthracene, or naphthalene may be used, and more preferably, benzene, aniline, or phenol may be used in consideration of economic feasibility.

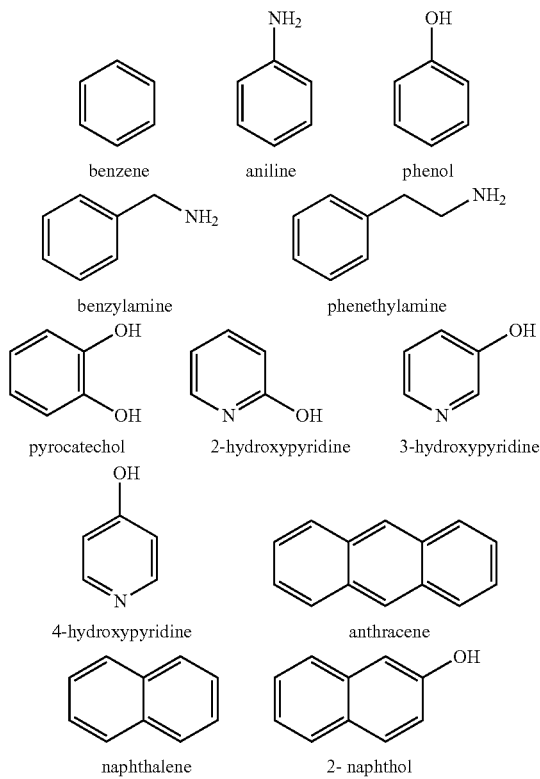

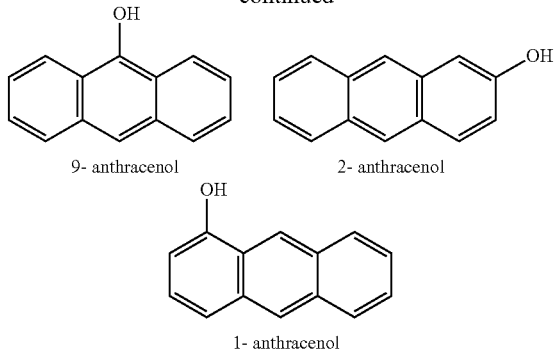

The polydopamine synthesized from such diverse sources may have unique properties corresponding to each thereof.

In an embodiment of the present invention, an aniline liquid phase precursor was used as the starting material.

The "aniline" used as the preferable starting material is $C_6H_5NH_2$, has a melting point of $-6.3°$ C., maintains a liquid state at room temperature, and has a merit of easy supplying in a gaseous state.

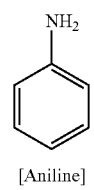

[Aniline]

Aniline may be commercially obtained via a hydrogenation reaction of nitrobenzene in the presence of a catalyst, via the reaction of chlorobenzene with ammonia, or by reducing nitrobenzene in an aqueous acid solution with an iron catalyst. The aniline which is a primary aromatic amine is weak base and reacts with an inorganic acid to form a salt. In an embodiment of the present invention, the aniline was used as the starting material.

Besides, the above-described other precursor materials of the catecholamines may be appropriately selected and used. For example, precursors such as benzene, pyrocatechol in which a hydroxyl functional group (—OH) is attached to a benzene ring, benzylamine and phenethylamine, in which each of one or two methylene bridges and one amine group are attached to a benzene ring, 2,3-dihydroxynaphthalene in which two hydroxyl functional groups are attached to sublimatable naphthalene, and 1-naphthylmethylamine in which an amine functional group is attached to naphthalene, may be used. In addition, by inducing a hydroxylation reaction or an amination reaction by controlling the plasma chemistry of benzene, cyclohexane, and a basic unit, a film of a mixture state of various kinds of catecholamines may be synthesized.

In particular, by using the materials easily synthesized or obtained by a person skilled in the art such as aniline as a starting material in the present invention, diverse merits of easy production and economic feasibility may be attained when compared to a case of using an extracted compound derived from living organisms such as DOPA.

Since DOPA, etc., which is commercially available in a powder shape requires a separate process for extraction from living organisms and is inconvenient and has high purchase price, mass-use for commercial purpose is somewhat difficult. However, in the case of using the starting material of the present invention, the catecholamines may be easily synthesized by a person skilled in the art and may be obtained by a more economic and convenient method.

Resulting Products

The target material obtained by plasma polymerization using the above-described starting materials is a catecholamine compound in the present invention.

"Catecholamine" means a monomolecule of a benzene ring having a hydroxyl group (—OH) as an ortho group and diverse alkylamines as a para group. Various derivatives thereof such as dopamine, dopamine-quinone, alpha-methyldopamine, norepinephrine, epinephrine, alphamethyldopa, droxidopa, and 5-hydroxydopamine may be included in the catecholamines. The most preferably, the dopamine is obtained as the target material.

It is known that the catecholamines having a catechol group may modify the surface of diverse materials (Haeshin Lee et al., Science 2007, 318, 426).

For example, during the oxidation of dopamine, electrons may leave to produce dopamine-quinone, and which may be converted to 3,4-dihydroxyindole (DHI) which is an important monomer for producing polydopamine. The DHI may be converted to a polymer shape and almost all materials in the periodic table may be coated therewith (FIG. 2).

Until now, the polydopamine has been prepared by a dip-coating method in an aqueous phase, of which reaction rate is slow and the surface obtained after coating may become uneven. That is, the surface roughness value may become undesirably large.

Synthetic Method: Plasma Polymerization

In the present invention, in order to synthesize catecholamines, not dip-coating but "plasma polymerization" is used with respect to the starting materials. In particular, the use of a dry plasma polymerization method is important characteristic.

Plasma is a gas which is ionized and electrically neutral as a whole, and the plasma used for the plasma polymerization is "low temperature plasma or cold plasma" which has high ionization degree, of which constituent elements are in a thermally equilibrium state, and the average temperature of which reaches tens of thousands degrees. The plasma may be easily obtained via the electrical discharge of a gas or an organic vapor in a low pressure state.

The low temperature plasma may be classified into three groups according to the kind of the gas and the vapor. The first group is the plasma of an inert gas, and chemical reactions are hardly performed in this plasma. The second group is the plasma of a simple reactive gas such as hydrogen, oxygen, nitrogen, carbon dioxide, etc., and the third group is the plasma of all the other gases and vapors for polymerization. By using plasma polymerization, the polymerization of an inert gas may be also performed.

The gas used in the present invention may be classified according to the function thereof into an activating/inert gas, a carrier gas, etc., and the gas may use an inert gas such as argon; and hydrogen, nitrogen, oxygen, vapor, ammonia, or a mixture thereof. Preferably, argon or nitrogen is used as the carrier gas; and at least one gas selected from the group consisting of air, hydrogen, oxygen, vapor and ammonia is used as the activating gas. More preferably, oxygen, argon or ammonia may be used, and the most preferably, oxygen may be used.

In particular, in the plasma polymerization process of the present invention, the use of oxygen as an effective activating gas is important characteristic.

Generally, in the case where oxygen is included in the activating gas in a plasma polymerization process, oxygen plasma has the property of easily etching a polymer, and a polymerization film itself may not be properly coated. In particular, in order to avoid the etching of an electrode part to which a power is applied due to the collision of cations/anions, thereby damaging a synthesized film, or to avoid the loss of an original structure due to the excessive fragmentation of a liquid precursor, a pulse power other than a continuous power may be used, or a substrate may be positioned at a place separated from plasma by a certain distance or may be earthen.

However, if oxygen is used as the activating gas in the polymerization process of the present invention, the thin film forming rate of the catecholamines at an RF electrode is faster rather than at the earthen part, and the catecholamines, for example, compounds similar to polydopamine were obtained much more. From the results, it is found that oxygen radicals or ions play an important role during synthesizing the polydopamine of multidimensional catecholamines from the basic structure of a catecholamine precursor during the dry plasma polymerization.

In the present invention, a "plasma polymerization process" means a process of growing catecholamines from molecules of a gas and organic vapor via consecutive activation-deactivation steps in a plasma state.

The plasma polymerization process in the present invention may be conducted in low pressure conditions of 1 torr or less, which is close to vacuum, preferably, $1 \times 10^{-3}$ to $5 \times 10^{-1}$ torr, preferably, $1 \times 10^{-2}$ to $5 \times 10^{-1}$ torr, more preferably, $1 \times 10^{-1}$ to $5 \times 10^{-1}$ torr, and the most preferably, $1 \times 10^{-1}$ torr.

In addition, the plasma polymerization process in the present invention may be conducted in radio frequency (RF) power conditions in a high frequency range of 0 to 200 W, preferably, 0 to 150 W, more preferably, 0 to 100 W, and further more preferably, 0 to 60 W.

It is obvious that a person skilled in the art may appropriately control the conditions of the plasma polymerization process according to the starting material used, the activating gas used, the temperature set, etc.

In the method of the present invention, polymer material catecholamine is produced while gases and vapors are converted to plasma in a low pressure state, and the surface of nearby solids is coated with the catecholamine in a thin film state. Therefore, the catecholamine molecules obtained by the method of the present invention may grow as a thin film at the surface of the nearby solids.

According to the method of the present invention, the effects of synthesizing catecholamine molecules and the surface modification of a solid may be attained at the same time.

In particular, plasma polymerization is one process from a basic material such as a gas and vapor to a final processing step, thus it is convenient. In addition, a pin hole free uniform coating may be obtained even though an ultra thin film is formed, and the polymerization may be performed even though a monomer does not include a functional group. Accordingly, the range of choice of a material to be coated is wide, any materials which are stable in vacuum or an atmospheric pressure may be used as the material to be coated, and good adhesiveness may be attained according to the properties of a catecholamine compound thus synthesized. Further, since a dry method is used, environmental contamination due to solvents is not generated, and ageing phenomenon generated during plasma surface treatment may be prevented.

The plasma polymerization reaction may be conducted in a gas state, however since a gas-solid collision ratio to a gas-gas collision ratio is high, and the deactivation of functional groups at the surface of a solid which may emit energy easily in a vacuum state, the plasma polymerization reaction may be mainly conducted at the surface of the solid, and molecules grown in the gas state may be adsorbed onto the surface of the solid. Therefore, the polymer material catecholamines thus synthesized may be grown on the surface of the solid as a thin film.

The deposition rate of the thin film composed of catecholamines may be from about tens to hundreds/min, and may be changed depending on the conditions of process variables such as the kind of the gas or vapor injected, the kind and shape of a reactor, the position and temperature of a solid (substrate), the flowing amount (F) of the gas, the pressure (P) of the gas, and a discharge power (W). Accordingly, it is obvious that a person skilled in the art may select and/or modify appropriate conditions for the present invention to implement the present invention referring to conventional techniques.

The thin film synthesized by the plasma polymerization of the present invention may additionally contain diverse hydrophilic functional groups in the basic structure of the catecholamine according to desired function so that various properties and function may be attained.

The catecholamine synthesized by the method may have a thin film thickness of about 0.01-2 μm, and a desired thickness may be obtained by appropriately controlling time conditions, etc. by a person skilled in the art.

In a preferred embodiment of the present invention, the polymerization reaction may be conducted in the RF power conditions of a high frequency range of 0-200 W, in pressure conditions of $1 \times 10^{-3}$ to $5 \times 10^{-1}$ torr, for about several minutes, for example, 1-100 minutes, more preferably, 1-60 minutes, or 1-30 minutes.

In an embodiment of the present invention, aniline was used as a precursor material, plasma polymerization conditions included an RF power of 50 W, and a deposition pressure of $1 \times 10^{-1}$ torr, oxygen, argon, or a mixture gas of oxygen and argon was used as an activating gas, a total gas flowing amount was adjusted to 20 sccm, and the gases were used after mixing in a certain ratio. After conducting the synthesis reaction for about 30 minutes, a thin film with a thickness of about 1 micrometer was obtained.

Plasma Polymerization Apparatus

Meanwhile, the method of the present invention may be implemented using an appropriate plasma polymerization apparatus.

In an embodiment for performing the present invention, the plasma polymerization apparatus of FIG. 1 mainly includes a reactor for generating plasma and a mixing bubbler for vaporizing and injecting a catecholamine precursor, and for heating/cooling (A in FIG. 1).

In the mixing bubbler (B in FIG. 1), a system used in the conventional metalorganic vapor phase epitaxy (MOCVD) is introduced, and a circulating water bath (<100° C.) for maintaining a constant temperature is included. The circulating water bath preferably maintains the temperature at 30-50° C. In addition, an electronic pressure control (EPC) is installed so that a carrier gas may make bubbles using a vaporized dopamine source to control the amount reaching the plasma reactor in a chamber constant.

Generally, a vapor pressure is sensitively dependent on the temperature and may be calculated by the following equation. In the case where the values of a and b are not known, the vapor pressure of the vaporized source may be indirectly obtained via the flowing amount of injected inert gas while maintaining the EPC pressure constant.

$$P_{Partial} = 10^{(a-b/T)} \times \frac{1013.25}{760} \text{mbar}$$

In an embodiment of the present invention, the vacuum degree of the plasma reactor is sufficiently decreased via pumping in the bubble making conditions of aniline, and the precursor is injected into a chamber with the vapor pressure of 40° C. at the temperature of 40° C. of the circulating water bath.

In the plasma polymerization process of the present invention using the above-described apparatus, catecholamine synthesis conditions via plasma polymerization on a two-dimensional substrate using a low pressure plasma process are established as the first step, and precursor fragments having a micro/nano size is three-dimensionally coated with catecholamine while synthesizing by a three dimensional nano CVD apparatus which additionally includes a powder feeder for supplying a catecholamine precursor powder which is a coating material, uniformly and quantitatively by the frequency, and a collector for efficiently and conveniently collecting fragments as the second step.

Synthesized Catecholamines

A catecholamine film formed by the plasma polymerization of the present invention has the following properties.

The catecholamine film formed by the plasma polymerization of the present invention has a rapid deposition rate when compared to a case of coating in an aqueous solution by a chemical reaction, and is eco-friendly and economic.

The surface energy of the catecholamine film formed by the plasma polymerization of the present invention may be freely controlled by adding a hydrophilic or hydrophobic gas to the reactor.

The surface of the film formed by the plasma polymerization of the present invention is very uniform without defects, however in the case where coating is performed in a liquid phase, the surface is rough and is present in a mass state. In a coating process according to the conventional dipping method in an aqueous solution, agglomeration phenomenon is generated, and a reaction rate is slow to produce uneven surface. However, in the present invention using the plasma polymerization process, the above-defects may not arise since the synthesis and coating processes are conducted in a plasma chamber in a rapid time.

PREFERRED EMBODIMENTS

Typical examples of the catecholamine synthesized in the present invention may be "dopamine".

Dopamine is a monomolecular material having catechol and an amine functional group, and a molecular weight of 153 (Da). It is known that in the case where a material of which surface is to be modified is injected into an aqueous dopamine solution having the same basic pH conditions (about pH 8.5) as the environment in the sea and then taken out after a certain time, a polydopamine (pDA) coating film is formed on the surface of a material by the oxidation of the catechol (FIG. 2).

Polydopamine (Formula 1) is an adhesive polymer imitating the adhesion mechanism of the adhesive protein of a mussel and is spontaneously produced via a polymerization reaction of dopamine in basic and oxidizing conditions. The polydopamine has good adhesiveness with the surface of various materials and recently receives attention as the component of a composite material.

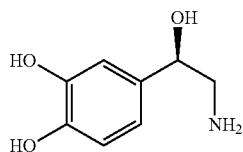

[Formula 1]

(In Formula 1, at least one of $R_1$, $R_2$, $R_3$, $R_4$ or $R_5$ is each independently at least one selected from the group consisting of thiol, primary amine, secondary amine, nitrile, aldehyde, imidazole, azide, halide, polyhexamethylene dithiocarbonate, hydroxyl, carboxylic acid, carboxylic ester and carboxamide, and the remainder of $R_1$, $R_2$, $R_3$, $R_4$ and $R_5$ is hydrogen)

However, dopamine forms a polydopamine coating film mainly via dipping in an alkaline liquid phase and oxidizing conditions until now. According to such a method, the application of dopamine may be partially limited; a mass production for industrialization may be difficult; an agglomeration phenomenon may be generated during the reaction, thus the surface may become rough.

However, since dopamine which has been used in the conventional liquid phase method is synthesized by dry plasma polymerization in the present invention, the present invention may be applied in various fields which may not use an aqueous solution, and the mass production thereof may be possible. In addition, the dopamine may have unique properties different from the dopamine synthesized in an aqueous solution. Further, the diverse surface functionalization according to the plasma method is possible, the present invention may be applied in diverse fields.

For example, in the method of the present invention, more uniform catecholamine coating may be introduced to the surface than by the conventional liquid phase coating method so that high reproducibility and stability of a bio adhesive and a hemostatic in a bio filed may be secured. In addition, a good structure of a conductive polymer film in diverse secondary batteries may be established in an energy field, and eco-friendly application having good adhesiveness in an environment field may be also possible.

MODE FOR CARRYING OUT THE INVENTION

Hereinafter, the present invention will be explained in more detail referring to exemplary embodiments. It will be obvious to a person skilled in the art that the embodiments are only for the illustration of the present invention and should not be interpreted to limit the scope of the present invention to the embodiments.

Synthesis was performed using the apparatus in FIG. 1.

Example 1: Synthesis of Polydopamine Using Plasma Polymerization (1) Selection of Precursor In order to synthesize polydopamine via plasma polymerization, two of a catechol (OH) functional group and an amine (NH2) functional group are required to be polymerized with a benzene ring which is a basic structure. The merit of the plasma polymerization of the present invention is that each of the functional groups could be formed in the benzene structure by controlling plasma chemical conditions.

An aniline liquid phase precursor in which an amine group is attached to a benzene structure was used among diverse precursors which have a dopamine basic structure and may be vaporized at a temperature lower than the controllable temperature of 100° C. by a circulating water bath.

(2) Plasma Polymerization Process Conditions

The using conditions of aniline bubbling are as follows. The vacuum state of the plasma reactor was sufficiently decreased by pumping, and valve 3 was opened at the circulating water bath temperature of 40° C. so as to inject the liquid phase precursor into the chamber by the vapor pressure of 40° C.

Then, valve 1 was opened so that 5 sccm of an argon gas was injected into the plasma reactor to obtain pressure conditions of $3.2 \times 10^{-2}$ torr, and in a state of injecting the argon gas into the chamber and the bubbler at the same time by opening valve 2, valve 1 was closed so that an argon carrier gas could supply the liquid phase precursor only via the interior of the bubbler to the plasma reactor (B in FIG. 1). This process order was set to avoid the momentary increase of the pressure in the chamber.

After that, activating gases such as air, $O_2$, and $NH_3$ were mixed through a gas pipe supplied into the chamber to fix a working pressure to $1.5 \times 10^{-1}$ torr, and a coating process was performed with an RF power of 0-200 W while performing a synthesizing process to a desired deposition thickness. If the coating was performed with 50 W for 30 minutes, the thickness of the coating was about 1 micrometer.

FIG. 4 illustrates the unique color of plasma according to the kind of gases. FIG. 4(a) corresponds to plasma color when the air and an argon gas are injected. Argon has violet color, however the air is partially mixed in the pressure of about $10^{-3}$ torr and has red color. FIG. 4(b) corresponds to plasma color for oxygen plasma, and FIG. 4(c) corresponds to plasma color when using an ammonia and ammonia/oxygen gas.

Hereinafter, the physical properties of the polydopamine synthesized by the dry plasma polymerization according to the present invention were evaluated.

In particular, an aniline liquid phase precursor was used, and plasma polymerization conditions were an RF power of 50 W and a deposition pressure of $1 \times 10^{-1}$ torr. Oxygen, argon, or a mixture gas of oxygen and argon was used as an activating gas, total gas flowing amount was controlled to 20 sccm, and the gases were mixed in a certain ratio. From the experimental results, the physical properties of each product obtained were evaluated.

(3) Control Group

As a control group for comparing the effects of the present invention, polydopamine was synthesized using the conventional liquid phase polymerization method.

Example 2: Thickness of Thin Film

The thickness of the plasma synthesized thin film was measured using a profilometer (α-step), and was measured after forming a step by attaching a tape on a silicon wafer substrate prior to the deposition.

FIG. 5 is a graph obtained by observing the thickness of a polymerized film after deposition under different plasma conditions with an RF power of 50 W for 30 minutes.

In the case where the argon, air, or ammonia gas was injected, similar results of about 1 micrometer thickness was obtained, and particularly, in the case where the oxygen gas was used, the polymerization rate increased at least twice. In a liquid state, about 3 hours were required for coating about 10 nm, while the deposition rate of the plasma polymerization was very fast by about a hundred times. Similar to the liquid polymerization, the plasma polymerization was promoted further in an oxygen atmosphere.

In addition, when comparing the thickness of the synthesized film at the ground where the collision of cations is not severe, the film at the electrode side had a further greater thickness and tended to be chemically activated. This characteristic is different from general characteristic by which a polymer may be easily etched in an oxygen atmosphere. Accordingly, the cations in the plasma are expected to play an important role in the polymerization reaction.

Example 3: Analysis of Physical Properties of Synthesized Polydopamine 3-1 FTIR

First, ATR FTIR analysis results under respective plasma conditions are shown in FIG. 6. Since the coated thickness was 1 μm or more, the absorbance in accordance with wavelengths was observed closely.

FIG. 6 is a graph obtained by analyzing through ATR FTIR, the chemical bonding state of a sample produced via dopamine plasma polymerization in various plasma gas conditions using an aniline liquid phase precursor. In order to complement the result interpretation, the FTIR results of a polydopamine solution polymerized in a liquid phase and a liquid aniline source are suggested together.

In consideration of only a dopamine monomer, peaks on the following bonds of C—H (3000-3100 cm$^{-1}$, stretch) detected from a benzene ring (aromatic ring), C—H (695 cm$^{-1}$:meta, 750 cm$^{-1}$:ortho, 830 cm$^{-1}$:para, OOP bend), C—C (1400-1500 cm$^{-1}$, 1585-1600 cm$^{-1}$, stretch), and C=C (1400-1600 cm$^{-1}$, stretch) according to the position of a functional group substituted at the benzene ring, catechol O—H (3300-3450 cm$^{-1}$ stretch), C—H (2870 cm$^{-1}$, 2950 cm$^{-1}$ stretch) from a chain type aliphatic structure, N—H (1560-1640 cm$^{-1}$, bend, 3250-3400 cm$^{-1}$, stretch) due to a primary amine, and C—N (1000-1350 cm$^{-1}$, stretch) were expected to be present.

Generally known polydopamine by liquid polymerization has typical FTIR peaks of N—H (1560-1640 cm$^{-1}$, bend, 3250-3400 cm$^{-1}$, stretch) due to a primary amine, and catechol O—H (3300-3450 cm$^{-1}$ stretch).

Such an aspect coincided with the FTIR analysis results of a polydopamine polymerization solution in a liquid state, and it was found that information on the primary amine and the catechol OH overlapped, and main FTIR peaks were present at two positions of 1637 cm$^{-1}$ and 3240 cm$^{-1}$.

The results were observed in the FTIR results of the plasma polymerization film of the present invention.

Near 3600 cm$^{-1}$, peaks concerning free OH stretching were appeared, in the broad range peaks around 3000 cm$^{-1}$ which were the results of the plasma polymerization film, information on chain type C—H (2870 cm$^{-1}$, 2950 cm$^{-1}$ stretch), benzene (aromatic) C—H (3000-3100 cm$^{-1}$, stretch), primary amine N—H (3250-3400 cm$^{-1}$, stretch), and catechol O—H (3300-3450 cm$^{-1}$ stretch) was shown in overlap.

In particular, the peak at 1637 cm$^{-1}$ due to the primary amine had the strongest intensity in the film synthesized only using oxygen plasma. From the result, the corresponding conditions were the most similar to those for the liquid phase plasma polymerization film.

Besides, information on C—H (695, 750, 830 cm$^{-1}$, stretch) according to the position (para, ortho, meta) of the functional group substituted at the benzene ring, and benzene C=C, C—N bond was shown in overlap. Particularly, prominent peaks of 1097, 1193, and 1409 cm$^{-1}$ in the oxygen plasma conditions showed the information of the bonds of C—C(in-plane vibration), C—O (asymmetric vibration), and C—H (bending), respectively. In particular, the presence of a peak around 3240 cm$^{-1}$ meant the synthesis of a film including catechol in oxygen plasma conditions.

As described above, by analyzing the FTIR results, it was found that a polydopamine structure was present.

3-2 Optical Properties (UV Visible Absorption)

Since optical properties may not be obtained by forming functional groups including oxygen or nitrogen by the simple plasma treatment of a surface, however form the inherent properties of a material, the production of a material may be identified by observing the absorbance thereof.

Generally, polydopamine polymerized in a liquid phase is known to have absorbance at the wavelengths of 280 nm and 350 nm (Q. Wei et al., Polym. Chem., 2010, 1, 1430-1433).

In the present invention, a film was polymerized in diverse plasma conditions using aniline as a liquid precursor, and the UV absorbance analysis results are shown in FIG. 7.

For aniline plasma polymerization film, two peaks at 280 nm and 350 nm were overlapped in all plasma conditions. From the results, it was found that similar UV absorbance was obtained for the film synthesized by the plasma polymerization of the present invention as for the known polydopamine. That is, polydopamine was secured to be successfully synthesized.

Further, it was found that the product of the present invention was quite different from a polyaniline (PANI) film polymerized using aniline. The UV absorbance peaks of the polyaniline were found at positions 327-365 nm and 600-620 nm and were confirmed to be quite different from the absorbance properties of the conventionally known polyaniline (Wolfgang maser et al., SPIE 2007). Accordingly, the product of the present invention was secured to be not polyaniline (PANT) but polydopamine.

3.3 XPS

In order to recognize the chemical bonding state of the plasma polymerization film thus synthesized, XPS analysis was performed with respect to polydopamine synthesized in a liquid phase and films synthesized in different plasma conditions, and the results are shown in the following table and FIG. 8.

TABLE 1

| RF power | Ref. | C | N | O | N/O | W.P | Precursors |
|---|---|---|---|---|---|---|---|
| | | 0.72 | 0.09 | 0.18 | 0.50 | | |
| 50 W | O$_2$ only | 0.61 | 0.15 | 0.24 | 0.63 | 1' 10$^{-1}$ | Aniline |
| | O$_2$/NH$_3$ | 0.69 | 0.15 | 0.16 | 0.94 | | |
| | NH$_3$ | 0.63 | 0.14 | 0.23 | 0.61 | | |
| | Ar only | 0.79 | 0.11 | 0.10 | 1.10 | | |

According to the XPS wide scan and quantitative analysis results of polydopamine synthesized using an aniline precursor, the peaks of carbon, nitrogen, oxygen were found under each of the plasma conditions (O$_2$ only, NH$_3$/O$_2$, NH$_3$ only, Ar only) (FIG. 8).

The basic formula of a dopamine monomer is C$_8$H$_{11}$NO$_2$, and the component ratio of polydopamine synthesized in a liquid phase is suggested as ref. in the above table. Similar conditions of the present invention suggested by a reference value of 0.5 included $O_2$ only and $NH_3$ only with the values of 0.63 and 0.61, respectively.

From the results, it is thought that polydopamine may more preferably be obtained in conditions of using $O_2$ only or $NH_3$ only, however nitrogen or oxygen functional group is etched in plasma conditions of using Ar only, and a graph in which a carbon component increases is obtained, thereby possibly synthesizing a dense polydopamine film in which the networking between oxygen, nitrogen and carbon is formed well.

That is, in the present invention, all $O_2$, $NH_3$ and Ar may be used in the plasma polymerization for synthesizing polydopamine, and $O_2$ may be the most preferable.

3.4 Surface Roughness (Profilometer)

Polydopamine synthesized in a liquid phase is known to have a rough surface, because agglomeration may be easily generated, and island growth may be attained instead of a continuous film formation during polymerizing dopamine in a liquid phase.

In order to analyze the surface roughness of a film polymerized using diverse plasma using aniline according to the present invention, surface roughness was measured in 1,000 μm (1 μm resolution) region using a profilometer (a step).

The results are shown in FIG. 9.

In the polydopamine film by the plasma polymerization of the present invention, a planar state was maintained such that the surface roughness thereof was similar to that of a Si wafer substrate during the growth from a nano-size thickness to a micro-size thickness.

Meanwhile, a polydopamine film synthesized in a liquid phase as a control group exhibited the roughness of three times that of the present invention even with a nano-size thickness. This aspect became severe with the increase of the thickness.

In addition, in order to compare the surface shape of a film synthesized in different plasma conditions with dopamine synthesized in a liquid phase, a cross-section was formed in the Si wafer, and HRSEM analysis was performed on the surface shape in an inclined angle.

As shown in FIG. 10, the film synthesized by plasma was found to have very planar surface similar to the Si wafer irrespective of magnification, however the dopamine film synthesized in a liquid phase was found to have very rough and lumpy surface.

From the results, it was found that the polydopamine synthesized by the plasma polymerization of the present invention had markedly small surface roughness.

3-5 Surface Energy Property (Contact Angle)

The contact angle (water) of a polydopamine coating is known to be 65 and have hydrophilic surface characteristic, and this is because a polar hydroxyl group including oxygen and a polar amine group are included.

The measured results of water contact angle for polydopamine synthesized by diverse plasma process conditions using an aniline liquid phase precursor according to the present invention are shown in FIG. 11.

A sample synthesized in oxygen plasma conditions had the lowest contact angle of about 14 degrees, and the contact angle increased according to the increase of the amount of the argon gas. In the case of using argon only, the contact angle of about 62 degrees was obtained, and this contact angle was similar to that of the polydopamine synthesized in a liquid phase as the control group. For reference, it was thought that a bare Si which was experimented together had a small contact angle because of a surface oxide layer.

From the results, the polydopamine film by the plasma polymerization of the present invention was secured to have a hydrophilic surface according to the conditions such as oxygen plasma.

3-6 Ag Precipitation (Metallization)

Generally, polydopamine synthesized in a liquid phase has precipitating property as a dopamine quinine shape by reducing cations in an aqueous solution on a surface according to the following reaction.

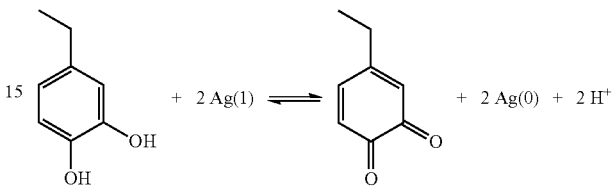

The polydopamine film by the plasma polymerization of the present invention was examined if it also had the above properties.

A polymerized film synthesized in a mixed plasma condition of oxygen and argon (15/5) was immersed according to the thickness (5, 10 nm, 1 μm) in 50 mL of an $AgNO_3$ solution, for 12 hours, and dried in a vacuum oven. After that, HRSEM analysis was performed, and polydopamine synthesized in a liquid phase was treated in the same conditions as a comparative sample.

From the results, as shown in FIG. 12, in the case where the thickness of the plasma polymerized polydopamine was small, similar Ag precipitation aspect as the polydopamine polymerized in a liquid phase was found. In particular, it was found that in the case where the thickness of the plasma polymerized polydopamine film was large, the size of the precipitated Ag increased further. Meantime, a reference sample obtained by attaching an OH functional group to an Si substrate by simple oxygen plasma or ozone treatment did not produce Ag precipitation by the test in the same conditions.

From the results, the polydopamine film by the plasma polymerization of the present invention was found to have a catechol (OH) functional group.

3-7 Measuring SIMS Image

Secondary ion mass spectrometry (SIMS) is a method of analyzing the chemical components and surface structure by detecting secondary ions produced during the collision of energy beam to the surface of a sample, and the chemical components and surface structure of the polydopamine by the plasma polymerization of the present invention were analyzed.

Results on polydopamines synthesized using the liquid phase precursor of benzylamine, penethylamine as well as aniline and in diverse plasma process conditions were overlapped with the SIMS result of dopamine in a liquid phase, and the SIMS result obtained using aniline as the liquid phase precursor in oxygen plasma conditions coincided with the result of the dopamine in a liquid phase (FIG. 13).

INDUSTRIAL APPLICABILITY

As described above, the present invention provides a novel method of effectively synthesizing a catecholamine compound not by the conventional dip-coating method but by a dry plasma polymerization process. According to the present invention, particularly, a synthesis rate is fast by a hundred times, and since a dry process is used, the present invention may be applied in various fields in which an aqueous solution cannot be used, and mass production is possible. The catecholamine has unique properties such as a very planar surface which is different from catecholamine (for example, dopamine) which is synthesized in an aqueous solution state, and diverse surface functionalization via plasma is possible. Therefore, the present invention may be usefully applied in a wide range including a bio filed, an energy filed, an environment field, etc.

The invention claimed is:

1. A thin film comprising a catecholamine having overlapping FTIR peaks representative of NH and OH functional groups and a UV absorption peak between 280 nm and 350 nm; wherein the film has a thickness of from 0.5 to 2 μm and a surface roughness of less than 10 Å.

2. The thin film of claim 1, wherein the thin film has a planar surface of the same degree as an Si wafer substrate.

3. The thin film of claim 1, wherein the catecholamine has an FTIR peak between 3250 to 3450 $cm^{-1}$.

4. The thin film of claim 1, wherein the catecholamine has an FTIR peak of 3240 $cm^{-1}$.

5. The thin film of claim 1, wherein the thin film has a thickness of 1 μm.

6. The thin film of claim 1, wherein the catecholamine is selected from the group consisting of dopamine, dopamine-quinone, alphamethyldopamine, norepinephrine, epinephrine, alphamethyldopa, droxidopa, and 5-hydroxydopamine.

7. The thin film of claim 1, wherein the catecholamine is polydopamine.

8. The thin film of claim 7, wherein the thin film has a thickness of 1 μm.

* * * * *